United States Patent
Osburn et al.

(10) Patent No.: US 10,788,480 B2
(45) Date of Patent: Sep. 29, 2020

(54) AGGREGATION-ASSISTED SEPARATION OF PLASMA FROM WHOLE BLOOD

(71) Applicant: THE JOHNS HOPKINS UNIVERSITY, Baltimore, MD (US)

(72) Inventors: William O. Osburn, Ellicott City, MD (US); Stuart C. Ray, Lutherville-Timonium, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 254 days.

(21) Appl. No.: 15/524,960

(22) PCT Filed: Nov. 6, 2015

(86) PCT No.: PCT/US2015/059402
§ 371 (c)(1),
(2) Date: May 5, 2017

(87) PCT Pub. No.: WO2016/073823
PCT Pub. Date: May 12, 2016

(65) Prior Publication Data
US 2017/0336387 A1 Nov. 23, 2017

Related U.S. Application Data

(60) Provisional application No. 62/076,814, filed on Nov. 7, 2014.

(51) Int. Cl.
| | | |
|---|---|---|
| *B01L 3/00* | (2006.01) | |
| *G01N 33/49* | (2006.01) | |
| *G01N 33/50* | (2006.01) | |
| *A61K 35/16* | (2015.01) | |
| *C12Q 1/04* | (2006.01) | |

(52) U.S. Cl.
CPC ........... *G01N 33/491* (2013.01); *A61K 35/16* (2013.01); *B01L 3/50273* (2013.01); *B01L 3/502753* (2013.01); *C12Q 1/04* (2013.01); *G01N 33/5002* (2013.01); *B01L 2300/0681* (2013.01); *B01L 2400/0406* (2013.01); *B01L 2400/0409* (2013.01); *G01N 2333/005* (2013.01); *G01N 2333/16* (2013.01); *G01N 2333/445* (2013.01); *G01N 2800/26* (2013.01); *Y02A 50/411* (2018.01)

(58) Field of Classification Search
None
See application file for complete search history.

(56) References Cited

U.S. PATENT DOCUMENTS

| | | | | |
|---|---|---|---|---|
| 4,246,107 | A * | 1/1981 | Takenaka | A61M 1/3633 210/259 |
| 4,987,085 | A | 1/1991 | Allen et al. | |
| 5,423,989 | A * | 6/1995 | Allen | C12Q 1/26 210/488 |
| 5,460,974 | A * | 10/1995 | Kozak | C12Q 1/60 422/412 |
| 5,766,552 | A | 6/1998 | Doshi et al. | |
| 8,003,407 | B2 | 8/2011 | Zhou et al. | |
| 2002/0036170 | A1* | 3/2002 | Harvey | G01N 33/558 210/656 |
| 2006/0029923 | A1* | 2/2006 | Togawa | B01D 61/18 435/2 |
| 2012/0118392 | A1* | 5/2012 | Blankenstein | G01N 33/491 137/1 |
| 2012/0164747 | A1* | 6/2012 | Choi | G01N 33/5094 436/175 |
| 2013/0137182 | A1 | 5/2013 | Choi et al. | |
| 2014/0263059 | A1 | 9/2014 | Burg et al. | |
| 2014/0295472 | A1* | 10/2014 | Shevkoplyas | G01N 33/526 435/13 |

FOREIGN PATENT DOCUMENTS

| | | | | |
|---|---|---|---|---|
| EP | 0597577 | | 5/1994 | |
| WO | WO-2013071301 | A1 * | 5/2013 | ........... G01N 33/526 |

OTHER PUBLICATIONS

Chen et al., "Microfluidic chip for plasma separation from undiluted human whole blood samples using low voltage contactless dielectrophoresis and capillary force," Lab Chip., 2014; 14(12): 1996-2001.
Songjaroen et al., "Blood separation on microfluidic paper-based analytical devices," Lab Chip., 2012; 12(18): 3392-8.
Wang et al., "Simple filter microchip for rapid separation of plasma and viruses from whole blood," Int J Nanomedicine, 2012; 7: 5019-28.
International Search Report and Written Opinion for Application No. PCT/US2015/059402 dated Feb. 29, 2016, 12 pages.
Yang X, et al. "Integrated separation of blood plasma from whole blood for microfluidic paper-based analytical devices", Lab Chip. 2012;12(2):274-80.

* cited by examiner

*Primary Examiner* — Bradley R Spies
(74) *Attorney, Agent, or Firm* — Casimir Jones, S.C.; Jeffrey W. Childers

(57) ABSTRACT

Methods for separating blood plasma from whole blood in the absence of performing centrifugation are provided. The method combines mechanical filtration and blood cell aggregation and is adapted for use in POC clinical testing.

29 Claims, 2 Drawing Sheets

AGGREGATION-ASSISTED SEPARATION OF PLASMA FROM WHOLE BLOOD

CROSS-REFERENCE TO RELATED APPLICATIONS

This application is a 35 U.S.C. § 371 National Stage Entry of International Application No. PCT/US15/059402 having an international filing date of May 29, 2015, which claims the benefit of U.S. Provisional Application No. 62/076,814, filed Nov. 7, 2014, the contents of which are incorporated herein by reference in their entirety.

BACKGROUND

Separation of plasma from cellular components in human blood can overcome problems with components, such as cells and/or substances they contain, which can inhibit assays. For example, red blood cells (RBCs) contain heme molecules that strongly inhibit downstream clinical assays, such as polymerase chain reaction (PCR)-based assays. Currently available methods for generating plasma of sufficient quality for use in clinical assays involve the application of centrifugal force to sediment cells. Such centrifugation is problematic for performing point-of-care (POC) clinical tests and presents significant hurdles for performing diagnostic testing in resource-limited settings. Development of an easy-to-use POC method to separate plasma from whole blood would allow for a cost effective and time efficient tool to obtain blood plasma for diagnostic testing in such settings.

SUMMARY

The presently disclosed subject matter generally provides a method for generating blood plasma of sufficient quality for use in POC clinical assays from whole blood rapidly and without requiring centrifugation.

In some aspects, the presently disclosed subject matter includes a combination of serial mechanical filtration with hemagglutination agent-mediated aggregation of red blood cells to provide blood plasma of sufficient purity for use in clinical assays. The presently disclosed methods overcome the requirement of using a centrifuge to collect plasma, can be used in a number of fluid delivery systems including, but not limited to, microfluidic systems, pump-driven systems, and the like, and can be performed in minutes. The aforementioned advantages make the presently disclosed methods particularly suitable for use in POC clinical tests. In certain aspects, the presently disclosed subject matter provides a method for generating blood plasma from whole blood, the method comprising: (a) applying a sufficient force to a whole blood sample to pass a fraction of the sample through a first filter to obtain a first filtrate comprising red blood cells (RBCs); (b) incubating a mixture of the first filtrate and a hemagglutination agent for a period of time sufficient for agglutination of the RBCs to occur in the first filtrate; and (c) applying a sufficient force to the incubated mixture of step b) to pass a fraction of the incubated mixture of step b) to obtain a second filtrate comprising blood plasma.

In certain aspects, the presently disclosed subject matter provides a method of conducting a blood test at the point-of-care, the method comprising: (a) generating blood plasma from a whole blood sample obtained from a patient in need of a blood test at the point-of-care, comprising: (i) applying a sufficient force to a whole blood sample to pass a fraction of the sample through a first filter to obtain a first filtrate comprising red blood cells (RBCs); (ii) incubating a mixture of the first filtrate and a hemagglutination agent for a period of time sufficient for agglutination of the RBCs to occur in the first filtrate; and (iii) applying a sufficient force to the incubated mixture of step b) to pass a fraction of the incubated mixture of step b) to obtain a second filtrate comprising blood plasma; and (b) using the blood plasma in a blood test at the point-of-care.

In certain aspects, the presently disclosed subject matter provides a method for generating blood plasma from whole blood, the method comprising: (a) providing a blood sample from a subject; (b) contacting the blood sample with a first filter and applying a sufficient force to the sample to push the sample through the first filter to obtain a first filtrate, wherein the first filtrate contains RBCs; (c) contacting the first filtrate with a second filter, adding an hemagglutination agent to the first filtrate and incubating the mixture of first filtrate and hemagglutination agent for a sufficient period of time; (d) applying a sufficient force to the incubated mixture of step (c) to push the incubated mixture of step (c) through the second filter to generate a second filtrate, wherein the second filtrate comprises blood plasma.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
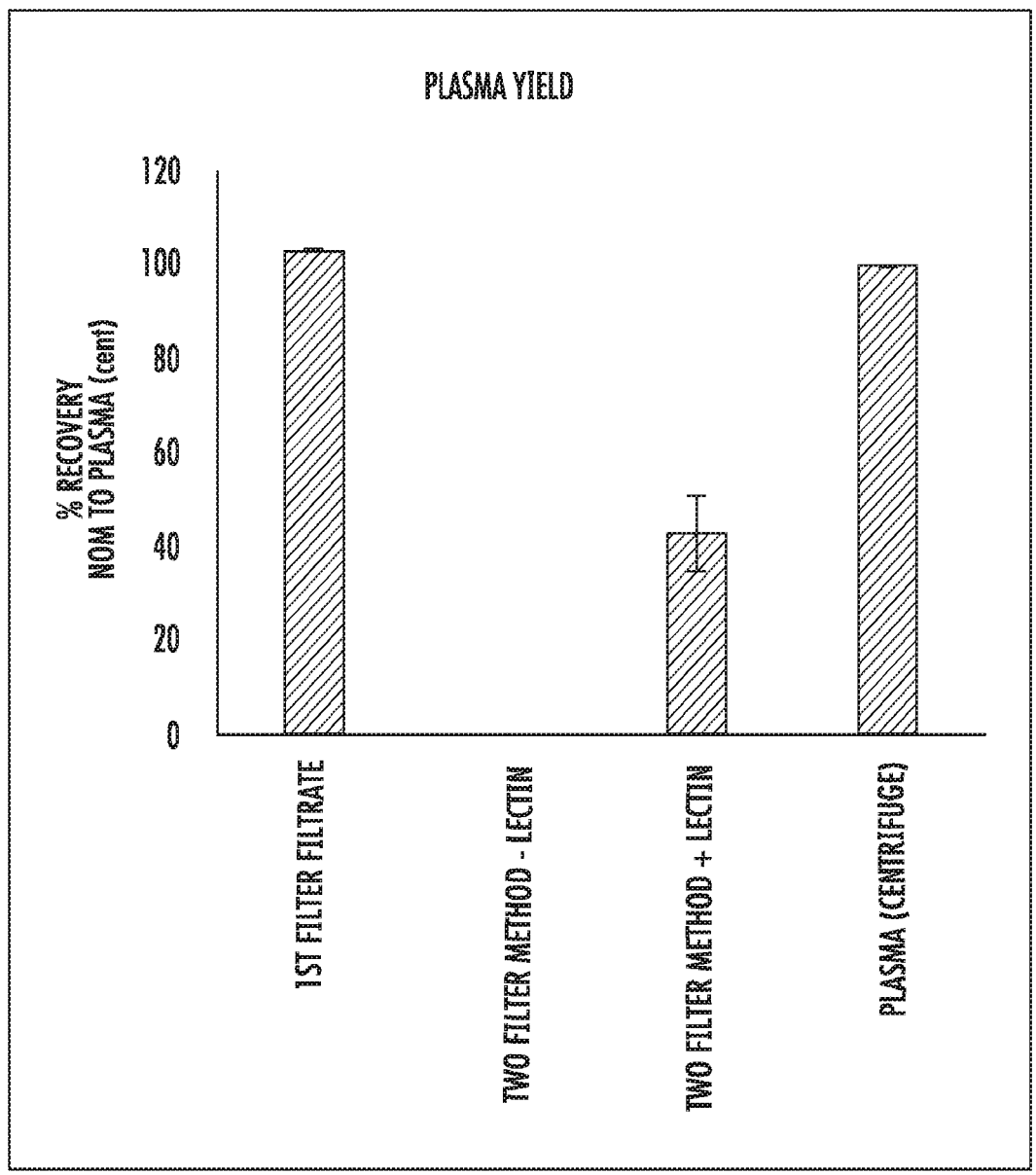
Figure 2:
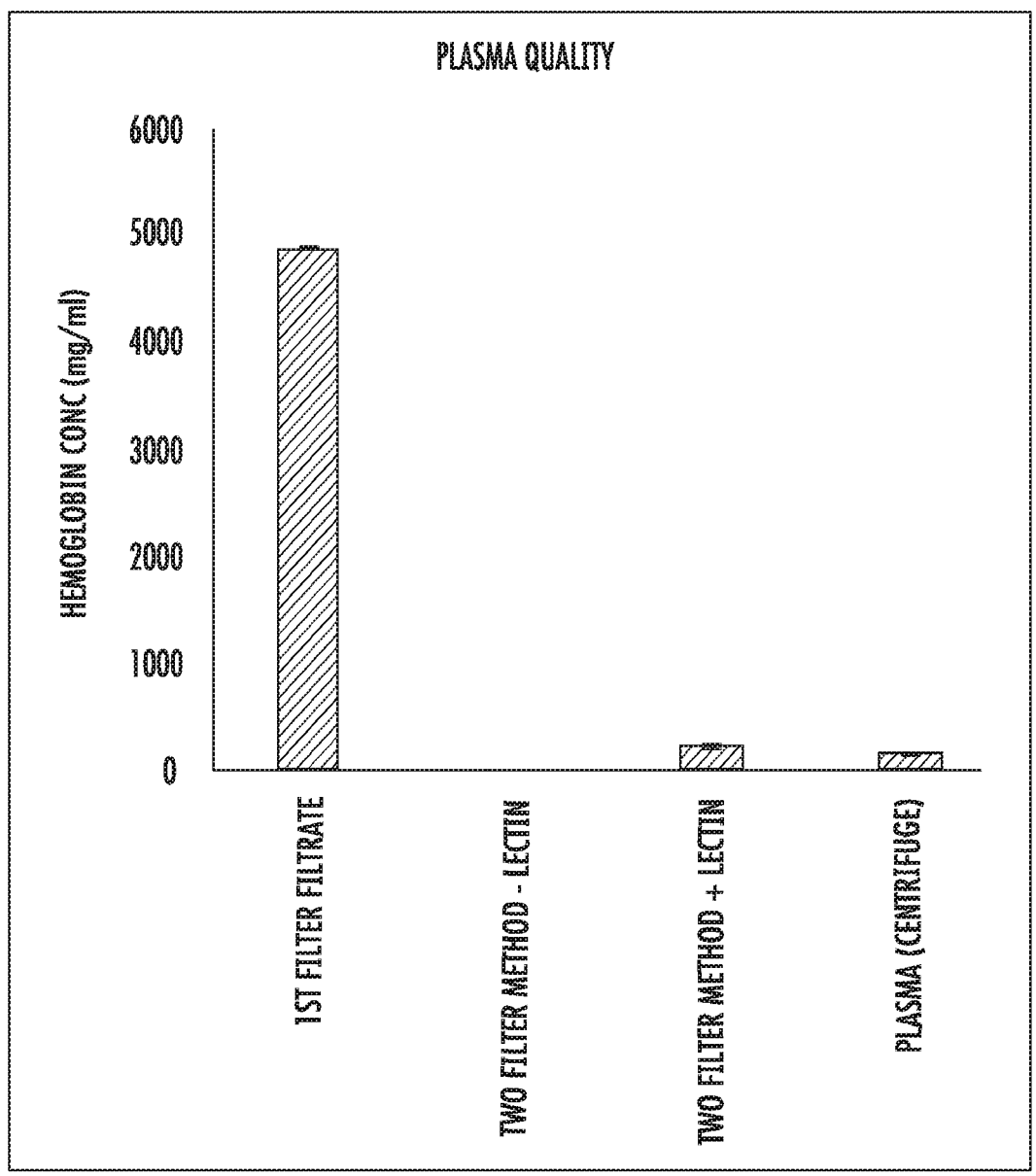

Having thus described the presently disclosed subject matter in general terms, reference will now be made to the accompanying Figures, which are not necessarily drawn to scale, and wherein:

FIG. 1 is a comparative plasma yield graph showing the plasma recovery using the presently disclosed methods and the plasma recovery obtained conventionally via centrifugation, after the first filtration, and after the second filtration with (+) or without (−) the use of concentrated lectin; and FIG. 2 is a comparative plasma quality graph showing the plasma quality using the presently disclosed methods and the plasma quality obtained conventionally via centrifugation, after the first filtration, and after the second filtration with (+) or without (−) the use of concentrated lectin.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Aggregation-assisted Separation of Plasma from Whole Blood

A. Background: Current Methods for Generating Plasma from Whole Blood without Centrifugation Existing non-centrifugal plasma separation filtration technologies have inherent limitations that preclude their use in next generation, silicon microchip-based clinical assays. A number of lateral flow filtration paper devices have been described that generate plasma for immediate use in subsequent assays (Yang 2012; Songjaroen 2012). These approaches separate blood cells from the plasma fraction based on size exclusion principles. Also, filtration-based approaches known in the art suffer from the necessity of the using a large surface area for filtration to limit filter backpressure. Such approaches fail to produce plasma of sufficient quality. For example, Wang et al. (2012) reported a filter paper-based plasma separation device that was only able to remove less than 85% of red blood cells and less than 90% of white blood cells. The remaining RBCs and WBCs in the plasma fraction produced by this method require further processing of the plasma before use in clinical assays.

Additional plasma generating devices have been described that utilize non-size exclusion methods. Dielectrophoresis also can be used to separate RBCs from plasma, but this approach is limited by poor plasma recovery and insufficient RBC removal (Chen 2014). Doshi, et al. (U.S. Pat. No. 5,766,552) describe a device that removes red blood cells from red blood cell-enriched solutions. In the method described by Doshi, et al., lectin is impregnated in an initial filter or coated on silica beads and used to form RBC clusters. Clusters are removed by the first filter, and a second filter is used to remove any RBCs that passed through the first filter.

B. Advantages of Point-Of-Care Testing and Current Applications Thereof

Point-of-care (POC) testing, or otherwise known as bedside testing, is defined as medical diagnostic testing performed outside the clinical laboratory in close proximity to where the subject is receiving care. Such POC testing is typically performed by non-laboratory personnel and the results are used for clinical decision-making.

Real-time blood analyzers are already widely used in POC diagnosis and treatment. Being able to analyze plasma that has been isolated from its whole blood source would prevent the need to send blood samples away to a laboratory to be centrifuged, therefore saving precious time in critical care situations.

Further, the ability to provide test results rapidly to the patient and/or healthcare provider is very important to impact outcomes of subjects having multiple diseases or conditions. Rapid tests to aid diagnosis and enable early detection of multiple diseases and physiologic conditions are being developed. Such tests are especially useful when they can be applied with self-testing and require little in the way of laboratory processing. Examples of POC test devices in common use today include pregnancy and fertility tests, as well as assays to monitor blood glucose in diabetics.

Development of diagnostic tests for infections that use POC testing are especially important in resource-poor settings; for this reason, POC testing has become a new goal to be achieved for infections, such as HIV, malaria, and hepatitis. Similarly, POC testing has the potential of impacting clinical outcomes when applied to infections that occur in the outpatient setting, not only by providing indications of disease, but by enabling development of more robust prevention algorithms.

C. Filtration Device and Methods of Use Thereof for Separating Plasma From Whole-Blood Accordingly, the presently disclosed matter provides methods for separating plasma from whole blood. The fundamental principle of the presently disclosed methods is size exclusion filtration. The methods described herein resolve numerous problems of non-centrifugal plasma separation filtration methods known in the art, including, but not limited to, poor quality plasma, poor plasma recovery, and insufficient RBC removal. The presently disclosed methods overcome these problems by utilizing serial mechanical filtration along with blood cell aggregation, the combination of which allows for plasma generation through the use of minimal force without requiring centrifugal force to drive the separation.

In a representative embodiment, the presently disclosed subject matter provides a method of generating blood plasma from whole blood, the method comprising: (a) applying a sufficient force to a whole blood sample to pass a fraction of the sample through a first filter to obtain a first filtrate comprising red blood cells (RBCs); (b) incubating a mixture of the first filtrate and a hemagglutination agent for a period of time sufficient for agglutination of the RBCs to occur in the first filtrate; and (c) applying a sufficient force to the incubated mixture of step b) to pass a fraction of the incubated mixture of step b) to obtain a second filtrate comprising blood plasma.

In a representative embodiment, the presently disclosed subject matter provides a method of conducting a blood test at the point-of-care, the method comprising: (a) generating blood plasma from a whole blood sample obtained from a patient in need of a blood test at the point-of-care, comprising: (i) applying a sufficient force to a whole blood sample to pass a fraction of the sample through a first filter to obtain a first filtrate comprising red blood cells (RBCs); (ii) incubating a mixture of the first filtrate and a hemagglutination agent for a period of time sufficient for agglutination of the RBCs to occur in the first filtrate; and (iii) applying a sufficient force to the incubated mixture of step b) to pass a fraction of the incubated mixture of step b) to obtain a second filtrate comprising blood plasma; and (b) using the blood plasma in blood test at the point-of-care.

In a representative embodiment, the presently disclosed methods include: (a) providing a blood sample from a subject; (b) contacting the blood sample with a first filter and applying a sufficient force to the sample to push the sample through the first filter to obtain a first filtrate, wherein the first filtrate contains RBCs; (c) contacting the first filtrate with a second filter, adding an hemagglutination agent to the first filtrate and incubating the mixture of first filtrate and hemagglutination agent for a sufficient period of time; (d) applying a sufficient force to the incubated mixture of step (c) to push the incubated mixture of (step c) through the second filter to generate a second filtrate, wherein the second filtrate is blood plasma.

In particular embodiments, the whole blood sample is obtained from a subject. The subject may have or be suspected of having an infection. For example, the subject may have or be suspected of having an infection selected from the group consisting of HIV, malaria, and hepatitis. Other infections for which rapid clinical point-of-care testing can be performed utilizing the presently disclosed methods are apparent to the skilled artisan. Low protein binding membranes known in the art are suitable for use with the presently disclosed methods. Representative examples of such membranes include, but are not limited to, cellulose acetate, silica-based filters (including on-chip features), polyethersulphone, polypropylene, and polyvinylidene difluoride. The first and the second filter can be made of the same or different materials (e.g., the same or different membrane can be used).

In particular embodiments, the first filter has a pore size that is equal to or greater than the pore size of the second filter. In particular embodiments, the first filter has a pore size that is greater than the pore size of the second filter. In particular embodiments, the pore size of the first filter ranges from about 2 μm to about 20 μm and has a surface area of about 0.2 cm$^2$ to about 0.8 cm$^2$, and the pore size of the second filter is about 2 μm or less and also can have a surface area of about 0.2 cm$^2$ to about 0.8 cm$^2$.

The presently disclosed subject matter contemplates incubating the first filtrate with varying concentrations (e.g., about 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1 mg/mL, etc.) of the hemagglutination agent (e.g., lectin, e.g., concentrated lectin) at ambient temperature (e.g., about 20° C., about 21° C., about 22° C., about 23° C., about 24° C., about 25° C.) for a period of time sufficient for agglutination of RBCs in the first filtrate to occur (e.g., less than about ten minutes).

In some embodiments, the first filtrate is incubated with the hemagglutination agent at ambient temperature for about 10 minutes or less. In some embodiments, the first filtrate is incubated with the hemagglutination agent at ambient temperature for about 9 minutes or less. In some embodiments, the first filtrate is incubated with the hemagglutination agent at ambient temperature for about 8 minutes or less. In some embodiments, the first filtrate is incubated with the hemagglutination agent at ambient temperature for about 7 minutes or less. In some embodiments, the first filtrate is incubated with the hemagglutination agent at ambient temperature for about 6 minutes or less. In some embodiments, the first filtrate is incubated with the hemagglutination agent at ambient temperature for about 5 minutes or less. In some embodiments, the first filtrate is incubated with the hemagglutination agent at ambient temperature for about 4 minutes or less. In some embodiments, the first filtrate is incubated with the hemagglutination agent at ambient temperature for about 3 minutes or less. In some embodiments, the first filtrate is incubated with the hemagglutination agent at ambient temperature for about 2 minutes or less. In some embodiments, the first filtrate is incubated with the hemagglutination agent at ambient temperature for about 1 minutes or less.

In some embodiments, the hemagglutination agent is incubated with the first filtrate prior to contacting the first filtrate with the second filter. In some embodiments, the hemagglutination agent is incubated with the first filtrate after contacting the first filtrate with the second filter. In some embodiments, the agglutination of RBCs in the first filtrate is achieved by the direct addition of concentrated lectin (concentration of about 0.1 mg/mL to about 1 mg/mL) to the first filtrate after contacting the first filtrate to the second filter.

In representative embodiments, the incubation time of the mixture comprising the first filtrate and the concentrated lectin is about 10 minutes or less at room temperature, e.g., about 20° C. to about 25° C.

In some embodiments, the force applied to the first and second filter is generated by standard microfluidic capillary flow. In more particular embodiments, the pore size of the first filter is about 5 μm and has a surface area of about 0.2 cm$^2$, and the pore size of the second filter is about 0.65 μm.

In some embodiments, applying the sufficient forces to the first filter and the second filter comprises applying a centrifugal force that is equivalent to the average force generated by microfluidic capillary flow. In some embodiments, applying the sufficient forces to the first filter and the second filter comprises applying a non-centrifugal force. In some embodiments, the first filtrate and the second filtrate are obtained in the absence of centrifugation. In some embodiments, the forces applied to the first filter and second filter are generated by an external pump system or by capillary flow in a microfluidic setup system. Accordingly, fluid delivery systems suitable for use with the presently disclosed methods include, but are not limited to, a microfluidic system, a pump driven system, and the like.

In some embodiments, the hemagglutination agent is a lectin (e.g., concentrated lectin). In particular embodiments, the lectin is selected from the group consisting of *Ricin communis*, *Datura stramonium*, *Phaseolus vulgaris*, *Wistera floribunda*, *Solanum tuberosum*, *Sambucus nigra*, *Pisum sativum*, *Lycopersicon esculentum*, *Lens culinaris*, *Maackia amurensis*, *Concanavalin A*, and *Aleuria aurantia*.

In some embodiments, the volume of whole blood sample ranges from about 10 μL to about 150 μL, making the presently disclosed matter a scalable method.

II. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The term "diagnosed," as used herein, refers to the recognition of a disease by its signs and symptoms (e.g., resistance to conventional therapies), or genetic analysis, pathological analysis, histological analysis, and the like.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Methods

In certain embodiments, 150 µL of whole blood is added to a 5-µm filter (0.2-cm² surface area) and a force generated by standard microfluidic capillary flow is applied to the sample to push the sample through the first filter. The first filtrate is removed and added to a second filter. This filter has a 0.65-µm pore size. A hemagglutination agent (*Ricin communis*, stock concentration, about 0.1 mg/mL to about 1 mg/mL) is added to the first filtrate, and the mixture is incubated for 10 min at room temperature. A force generated by standard microfluidic capillary flow is applied to the aforementioned mixture to push it through the second filter, to obtain a second filtrate.

More particularly, the following representative protocol can be used:

1. 150 μL of whole blood is added to a 5-μm filter (0.2 $cm^2$ surface area) and a force is applied to sample to push the sample through filter:
   a. For the initial experiment, a centrifugal force (600×g) was applied. This force is the average force generated by standard microfluidic capillary flow. This force also could be applied by an external pump or driven by capillary flow in a microfluidic setup.
   b. Multiple filter pore sizes (about 2 μm to about 20 μm) and surface areas (about 0.3 $cm^2$) will be evaluated.
   c. Non-RBCs are removed from the plasma at this step.
2. Filtrate is removed and added to the second filter. This filter has a 0.65-μm pore size and can have a surface area of about 0.2 $cm^2$ to about 0.8 $cm^2$.
3. Concentrated lectin (stock concentration, 0.1 to 1 mg/mL) is added to the filtrate of the first filter. *Ricin communis* lectin is suitable for use with the presently disclosed methods. Lectins from the following species will also be tested for improved yield/purity/flow: *Datura stramonium, Phaseolus vulgaris, Wistera floribunda, Solanum tuberosum, Sambucus nigra, Pisum sativum, Lycopersicon esculentum, Lens culinaris, Maackia amurensis, Concanavalin A*, and *Aleuria aurantia*.
4. Incubated for 10 min at room temperature. Shorter times will be evaluated, with the goal of getting the time down to less than one minute.
5. A force is applied to sample to push sample through filter.
   a. For the initial experiment, a centrifugal force (600×g) was applied. This force is the average force generated by standard microfluidic capillary flow. Thus, this force also could be applied by an external pump or driven by capillary flow in a microfluidic setup.
   b. Multiple filter pore sizes (about 0.65 μm to about 2 μm) will be evaluated.
   c. RBCs are removed from the plasma at this step.
6. The plasma generated in this step is suitable for use in clinical assays.

Example 2

Results and Discussion

Both WBC and RBC were removed during this process. White blood cells (WBCs) were removed during the first filtration and red blood cells (RBCs) during the second filtration to an extent similar to centrifugal separation (as measured by hemoglobin concentration).

Referring to FIG. 1, the plasma yield obtained using the presently disclosed method is compared to the plasma yield obtained conventionally via centrifugation, after the first filtration, and after the second filtration step with or without the use of a hemagglutination agent (e.g., concentrated lectin). As shown in FIG. 1, no volume of plasma is recovered when using two filtration steps without the use of concentrated lectin, whereas 100% of the volume of plasma is recovered in the first filtrate and about 43% of the volume of plasma that is obtained conventionally via centrifugation is recovered when using the presently disclosed method using an unoptimized surface.

Referring now to FIG. 2, the quality of plasma obtained using the present disclosed method is compared to the quality of plasma obtained conventionally via centrifugation, after the first filtration, and after second filtration step with or without the use of a hemagglutination agent (e.g., concentrated lectin). The plasma quality graph demonstrates that the current unoptimized methods provide comparable (e.g., equivalent) plasma quality to centrifugal methods known in the art.

The presently disclosed methods overcome the requirement of using a centrifuge to collect plasma, can be used in a number of fluid delivery systems including, but not limited to, microfluidic systems, pump-driven systems, and the like, is scalable, and can be performed in minutes. The aforementioned advantages make the presently disclosed methods particularly suitable for use in POC clinical tests.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Chen C C, et al. Microfluidic chip for plasma separation from undiluted human whole blood samples using low voltage contactless dielectrophoresis and capillary force. *Lab Chip*. 2014; 14 (12):1996-2001.

Songjaroen T, et al. Blood separation on microfluidic paper-based analytical devices. *Lab Chip*. 2012; 12 (18): 3392-8.

Wang S, et al. Simple filter microchip for rapid separation of plasma and viruses from whole blood. *Int J Nanomedicine*. 2012; 7:5019-28.

Yang X, et al. Integrated separation of blood plasma from whole blood for microfluidic paper-based analytical devices. *Lab Chip*. 2012; 12 (2):274-80.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for generating blood plasma from whole blood, the method comprising:
   a) applying a force of about 600×g to a whole blood sample to pass a fraction of the sample through a first filter to obtain a first filtrate comprising red blood cells (RBCs);
   b) incubating a mixture of the first filtrate and a hemagglutination agent for a period of time sufficient for agglutination of the RBCs to occur in the first filtrate; and
   c) applying a force of about 600×g to the incubated mixture of step b) to pass a fraction of the incubated mixture of step b) through a second filter to obtain a second filtrate comprising blood plasma, wherein the method does not comprise the use of centrifugation.

2. The method of claim 1, wherein the whole blood sample is obtained from a subject.

3. The method of claim 2, wherein the subject has or is suspected of having an infection.

4. The method of claim 3, wherein the infection is selected from the group consisting of HIV, malaria, and hepatitis.

5. The method of claim 1, wherein a volume of the whole blood sample ranges between about 10 µL to about 150 µL.

6. The method of claim 1, wherein the first filter has a pore size that is equal to or greater than the pore size of the second filter.

7. The method of claim 1, wherein the first filter has a pore size ranging from about 2 µm to about 20 µm and a surface area ranging from about 0.2 to about 0.8 cm$^2$.

8. The method of claim 1, wherein the second filter has a pore size of about 2 µm or less and a surface area ranging from about 0.2 to about 0.8 cm$^2$.

9. The method of claim 1, wherein the first filter has a pore size that is greater than the pore size of the second filter.

10. The method of claim 1, wherein the first filter has a pore size of about 5 µm and has a surface area of about 0.2 cm$^2$, and wherein the second filter has a pore size of about 0.65 µm and a surface area up to about 0.8 cm$^2$.

11. The method of claim 1, wherein a concentration of the hemagglutination agent incubated in the mixture ranges from about 0.1 mg/mL to about 1 mg/mL.

12. The method of claim 1, wherein the forces applied to the first filter and the second filter are generated by an external pump system.

13. The method of claim 1, wherein the forces applied to the first and the second filter are generated by capillary flow in a microfluidic setup system.

14. The method of claim 1, wherein the hemagglutination agent is a lectin.

15. The method of claim 14, wherein the lectin is selected from the group consisting of *Ricin communis, Datura stramonium, Phaseolus vulgaris, Wistera floribunda, Solanum tuberosum, Sambucus nigra, Pisum sativum, Lycopersicon esculentum, Lens culinaris, Maackia amurensis, Concanavalin A*, and *Aleuria aurantia*.

16. The method of claim 14, wherein the lectin is *Ricin communis*.

17. The method of claim 14, wherein the lectin is *Datura stramonium*.

18. The method of claim 1, wherein the first filtrate is incubated with the hemagglutination agent at ambient temperature for about 10 minutes or less.

19. The method of claim 1, wherein a volume of blood plasma recovered is at least about 43% of the volume of plasma that is obtained by conventional centrifugation methods.

20. The method of claim 1, wherein the quality of the blood plasma recovered is comparable to or better than the quality of blood plasma obtained by conventional centrifugal methods.

21. A method of conducting a blood test at the point-of-care, the method comprising:
   a) generating blood plasma from a whole blood sample obtained from a patient in need of a blood test at the point-of-care, comprising:
      i) applying a force of about 600×g to a whole blood sample to pass a fraction of the sample through a first filter to obtain a first filtrate comprising red blood cells (RBCs);

ii) incubating a mixture of the first filtrate and a hemagglutination agent for a period of time sufficient for agglutination of the RBCs to occur in the first filtrate; and iii) applying a force of about 600×g to the incubated mixture of step ii) to pass a fraction of the incubated mixture of step ii) through a second filter to obtain a second filtrate comprising blood plasma; and b) using the blood plasma in a blood test at the point-of-care, wherein the method does not comprise the use of centrifugation.

22. The method of claim 21, wherein the patient has or is suspected of having an infection.

23. The method of claim 22, wherein the infection is selected from the group consisting of HIV, malaria, and hepatitis.

24. The method of claim 21, wherein the first filter has a pore size ranging from about 2 µm to about 20 µm and a surface area ranging from about 0.2 to about 0.8 cm$^2$, and wherein the second filter has a pore size of about 2 µm or less and a surface area ranging from about 0.2 to about 0.8 cm$^2$.

25. The method of claim 21, wherein the first filter has a pore size of about 5 µm and has a surface area of about 0.2 cm$^2$, and wherein the second filter has a pore size of about 0.65 µm and a surface area up to about 0.8 cm$^2$.

26. The method of claim 21, wherein a concentration of the hemagglutination agent incubated in the mixture ranges from about 0.1 mg/mL to about 1 mg/mL, and wherein the hemagglutination agent is a concentrated lectin selected from the group consisting of *Ricin communis, Datura stramonium, Phaseolus vulgaris, Wistera floribunda, Solanum tuberosum, Sambucus nigra, Pisum sativum, Lycopersicon esculentum, Lens culinaris, Maackia amurensis, Concanavalin A*, and *Aleuria aurantia*.

27. The method of claim 21, wherein the forces applied to the first filter and the second filter are generated by an external pump system or capillary flow in a microfluidic setup system.

28. The method of claim 21, wherein the first filtrate is incubated with the hemagglutination agent at ambient temperature for about 10 minutes or less.

29. The method of claim 21, wherein a volume of blood plasma recovered is at least about 43% of the volume of plasma that is obtained by conventional centrifugation methods.

\* \* \* \* \*